United States Patent
Lynch

(10) Patent No.: US 8,690,923 B2
(45) Date of Patent: Apr. 8, 2014

(54) BONE FIXATION SYSTEMS AND METHODS

(75) Inventor: Bobby S. Lynch, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 364 days.

(21) Appl. No.: 12/892,660

(22) Filed: Sep. 28, 2010

(65) Prior Publication Data

US 2012/0078306 A1    Mar. 29, 2012

(51) Int. Cl.
*A61B 17/70*    (2006.01)

(52) U.S. Cl.
USPC ............ 606/260; 606/246; 606/265; 606/280

(58) Field of Classification Search
USPC ................................ 606/246–272; 623/17.15
See application file for complete search history.

(56) References Cited

U.S. PATENT DOCUMENTS

| | | | |
|---|---|---|---|
| 3,433,510 A * | 3/1969 | Hulterstrum | 403/77 |
| 5,800,435 A * | 9/1998 | Errico et al. | 606/261 |
| 7,909,852 B2 | 3/2011 | Boomer et al. | |
| 8,109,974 B2 | 2/2012 | Boomer et al. | |
| 2005/0288669 A1 * | 12/2005 | Abdou | 606/61 |
| 2011/0245874 A1 | 10/2011 | Boomer et al. | |

* cited by examiner

*Primary Examiner* — Nicholas Woodall
(74) *Attorney, Agent, or Firm* — Meyertons, Hood, Kivlin, Kowert & Goetzel, P.C.; Eric B. Meyertons

(57) ABSTRACT

In some embodiments, provided is an apparatus including a first elongated member, the first elongated member including a distal end and a proximal end. The distal end of the first elongated member is coupled to a first bone portion during use. The apparatus further includes a second elongated member including a distal end and a proximal end. The distal end of the second elongated member is coupled to a second bone portion during use. The proximal end of the second elongated member comprises a surface that is shaped complementary to a surface of the proximal end of the first elongated member. The apparatus still further includes a locking mechanism coupling the proximal end of the first elongated member to the proximal end of the second elongated member. The locking mechanism is adjustable from an unlocked position to a locked position such that, when the locking mechanism is in the unlocked position, the first elongated member is angularly movable relative to the second elongated member, and when the locking mechanism is in the locked position, the complementary shaped surfaces of the first elongated member and the second elongated member are directly connected and the relative angular position of the first elongated member and the second elongated member is substantially fixed.

18 Claims, 4 Drawing Sheets

BONE FIXATION SYSTEMS AND METHODS

BACKGROUND

1. Field of the Invention

The present invention relates to the field bone fixation. In particular, embodiments relate to spinal fixation systems and methods of use thereof.

2. Description of the Related Art

Spinal fusion is a surgical technique in which one or more spinal vertebrae are joined together such that relative motion no longer occurs between them. This technique is commonly used as treatment for fractured vertebrae, spinal deformities, spinal instability, and cervical disc herniations. In many cases, spinal fusion includes bone grafting followed by spinal immobilization. The bone grafting procedure generally includes placing pieces of bone (or bone substitute) between the vertebrae to be fused. Bone grafting, however, does not immediately fuse the vertebrae; instead, bone grafting stimulates the patient's body to grow new bone between the vertebrae. After bone grafting, the vertebrae are held fixed together, or immobilized, in order to allow growth of the new bone.

Various spinal fixation systems and methods are used to immobilize vertebrae after bone grafting. Many of these systems include at least one deformable rod for coupling portions of bone on either side of the vertebrae to be immobilized. The rod is often contoured by hand to fit the anatomy of the patient at the time of surgery. Extensive contouring of the rod during surgery, however, may significantly increase the operating time of the procedure and thus, increase the risk of serious postoperative complications. Furthermore, hand contouring of the rod is often an imprecise technique.

Other systems often include at least two rods having a distal and proximal end. The respective proximal ends of the rods are coupled by a locking mechanism and the respective distal ends are coupled to portions of bone on either side of the vertebrae to be immobilized. The locking mechanisms used in many of these systems require multiple fasteners and often limit the range of relative angulation between the rods. As such, the surgical procedure becomes more complicated and the spinal fixation system becomes less adaptable to the anatomy of the patient. Furthermore, the joint formed by the locking mechanism and the coupled proximal ends of the rods are often relatively bulky and may inflict additional postoperative injury and/or pain on the patient.

In view of these and other concerns, a spinal fixation system that is adaptable to the anatomy of a patient and easily implanted during surgery may be desired.

SUMMARY

Various embodiments of bone connection systems and related apparatus, and methods of operating the same are described. In some embodiments, provided is an apparatus including a first elongated member, the first elongated member including a distal end and a proximal end. The distal end of the first elongated member is coupled to a first bone portion during use. The apparatus further includes a second elongated member including a distal end and a proximal end. The distal end of the second elongated member is coupled to a second bone portion during use. The proximal end of the second elongated member comprises a surface that is shaped complementary to a surface of the proximal end of the first elongated member. The apparatus still further includes a locking mechanism coupling the proximal end of the first elongated member to the proximal end of the second elongated member. The locking mechanism is adjustable from an unlocked position to a locked position such that, when the locking mechanism is in the unlocked position, the first elongated member is angularly movable relative to the second elongated member, and when the locking mechanism is in the locked position, the complementary shaped surfaces of the first elongated member and the second elongated member are directly connected and the relative angular position of the first elongated member and the second elongated member is substantially fixed.

In some embodiments, provided is an apparatus including a first elongated member, the first elongated member including a distal end and a proximal end. The apparatus further includes a second elongated member including a distal end and a proximal end. The surface of the proximal end of the first elongated member is substantially convex and the surface of the proximal end of the second elongated member is substantially concave. The apparatus still further includes a locking mechanism coupled to the proximal end of the first elongated member and the proximal end of the second elongated member. The locking mechanism comprises a body and a co-axially coupled securing member. The body and securing member comprise respective openings defining respective internal spaces, the proximal end of the first elongated member being disposed in the internal space of the body and the proximal end of the second elongated member being disposed in the internal space of the securing member. The securing member is adjustable from an unlocked position to a locked position such that, when the securing member is in the unlocked position, the first elongated member and/or the second elongated member is angularly movable relative to the other elongated member, and when the securing member is in the locked position, the substantially concave and convex surfaces of the first elongated member and the second elongated member are directly connected and the relative angular position of the first elongated member and the second elongated member is substantially fixed.

In some embodiments, provided is a bone fixation kit including a plate coupled to a first bone portion during use. The bone fixation kit further includes a first elongated member including a distal end and a proximal end. The distal end of the first elongated member is coupled to the plate during use. The bone fixation kit still further includes a second elongated member including a distal end and a proximal end. The distal end of the second elongated member is coupled to a second bone portion during use. The proximal end of the second elongated member comprises a surface that is shaped complementary to a surface of the proximal end of the first elongated member. The bone fixation kit still further includes a locking mechanism coupled to the proximal end of the first and second elongated members during use. The locking mechanism is adjustable from an unlocked position to a locked position such that, when the locking mechanism is coupled to the proximal end of both the first and second elongated members and in the unlocked position, the first elongated member and/or the second elongated member is angularly movable relative to the other elongated member, and when the locking mechanism is coupled to the proximal end of both the first and second elongated members and in the locked position, the complementary shaped surfaces of the first elongated member and the second elongated member are directly connected and the relative angular position of the first elongated member and the second elongated member is substantially fixed.

In some embodiments, provided is an occipital cervical fixation kit including an occipital plate coupled to a first bone portion during use. The first bone portion is located substantially within the occipital region of the skull. The occipital cervical fixation kit further includes a first elongated member including a distal end and a proximal end. The distal end of the first elongated member is coupled to the occipital plate during use. The occipital cervical fixation kit still further includes a second elongated member including a distal end and a proximal end. The distal end of the second elongated member is coupled to a second bone portion during use. The second bone portion is located substantially within the vertebral column. The proximal end of the second elongated member comprises a surface that is shaped complementary to a surface of the proximal end of the first elongated member. The occipital cervical fixation kit still further includes a locking mechanism coupled to the proximal end of the first and second elongated members during use. The locking mechanism is adjustable from an unlocked position to a locked position such that, when the locking mechanism is coupled to the proximal end of both the first and second elongated members and in the unlocked position, the first elongated member and/or the second elongated member is angularly movable relative to the other elongated member, and when the locking mechanism is coupled to the proximal end of both the first and second elongated members and in the locked position, the complementary shaped surfaces of the first elongated member and the second elongated member are directly connected and the relative angular position of the first elongated member and the second elongated member is substantially fixed.

In some embodiments, provided is a method of coupling bone portions including coupling the proximal end of a first elongated member to the proximal end of a second elongated member such that the first elongated member and/or the second elongated member is angularly movable in three planes relative to the other elongated member. The method further includes coupling the distal end of the first elongated member to a first bone portion. The method still further includes angularly adjusting the second elongated member with respect to the first elongated member such that the second elongated member is positioned at a selected angular position relative to the first elongated member. The method still further includes directly connecting the proximal end of the second elongated member to the proximal end of the first elongated member. The proximal end of the second elongated member comprises a surface that is shaped complementary to a surface of the first elongated member. The method still further includes coupling the proximal end of the first elongated member to the proximal end of the second elongated member inhibits relative movement between the first elongated member and the second elongated member.

In further embodiments, additional features may be added to the specific embodiments described herein.

BRIEF DESCRIPTION OF THE DRAWINGS

The present invention will be better understood and other advantages will appear on reading the detailed description of some embodiments taken as non-limiting examples and illustrated by the following drawings in which.

Figure 1:
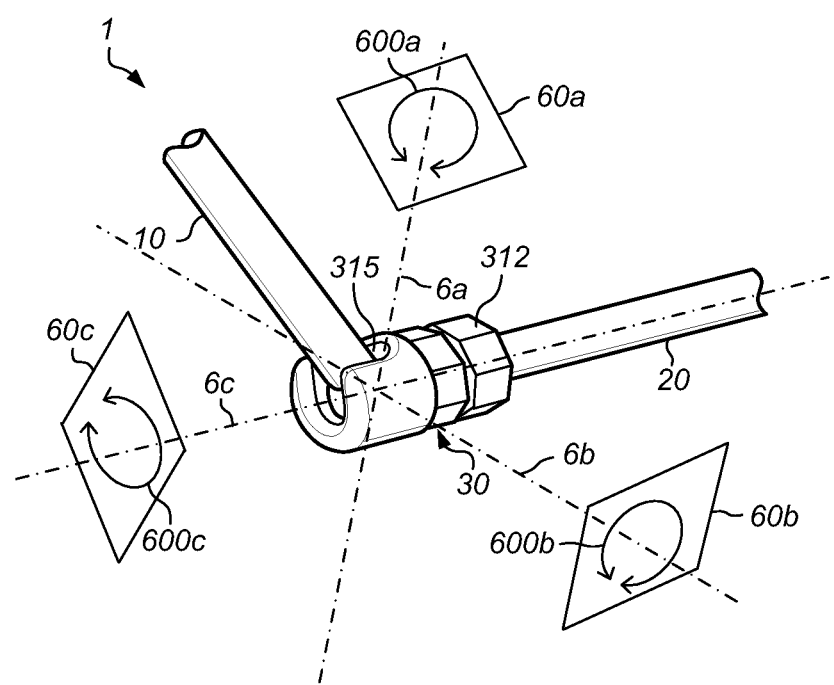
FIG. 1 is a perspective view of an adjustable linkage in accordance with one or more embodiments of the present technique.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF ILLUSTRATIVE EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a rod" may include a combination of two or more rods. Furthermore, the word "may" is used throughout this application in a permissive sense (i.e., having the potential to, being able to), not in a mandatory sense (i.e., must). The term "include," and derivations thereof, mean "including, but not limited to." Terms relating to orientation, such as "upper", "lower", "top", "bottom", "left", or "right", are used for reference only; the device herein may be used in any orientation. The order of any method may be changed, and various elements may be added, reordered, combined, omitted, modified, etc.

In the context of this application, the following terms are defined as:

"Coupled" means either a direct connection or an indirect connection (e.g., one or more intervening connections) between one or more objects or components. The phrase "directly connected" means a direct connection between objects or components such that the objects or components are connected directly to each other so that the objects or components operate in a "point of use" manner.

A "mechanical fastener" refers to a fastener that is used to couple two or more elements together by mechanical/physical force. Examples of a mechanical fastener include, but are not limited to, a bolt, a bone screw, a pin, a rivet, a wire, and any combination of such elements.

A "member" refers to a constituent part of a system. A "member" may include a plate, link, rod, or other structure of various sizes, shapes, and forms. A member may be a single component or a combination of components coupled to one another. A member may have various regular or irregular shapes. For example, portions of a member may be straight, curved, or a combination of both.

A "body" refers to any physical structure capable of at least partially supporting another object. A body may have various regular or irregular shapes. For example, portions of a body may be straight, curved, or a combination of both.

An "opening" refers to an aperture, such as a hole, gap, slit, or slot.

The term "elongated" means having more length than width.

An "elongated member" refers to any member of the system or apparatus having more length than width.

The term "locking mechanism" refers to a fastening device capable of coupling one or more objects to an external structure or one another.

The term "flange" refers to a projecting rim, collar, or ring on an elongated member cast or formed to give additional strength or to provide a place for attachment of other objects.

The term "proximal" refers to the portion of a structure which is closest to a point of reference.

The term "distal" refers to the portion of a structure which is furthest from a point of reference.

The term "superior" means being situated above an object.

The term "inferior" means being situated below an object.

The term "anterior" means being situated in front of an object.

The term "posterior" means being situated behind an object.

Figure 2A:
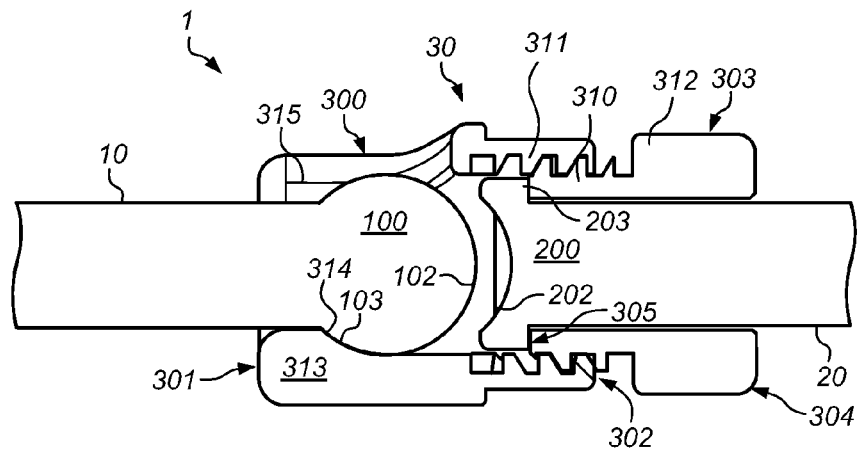
FIG. 2A is a cross-sectioned side view of an adjustable linkage depicted in an unlocked position in accordance with one or more embodiments of the present technique.
Figure 2B:
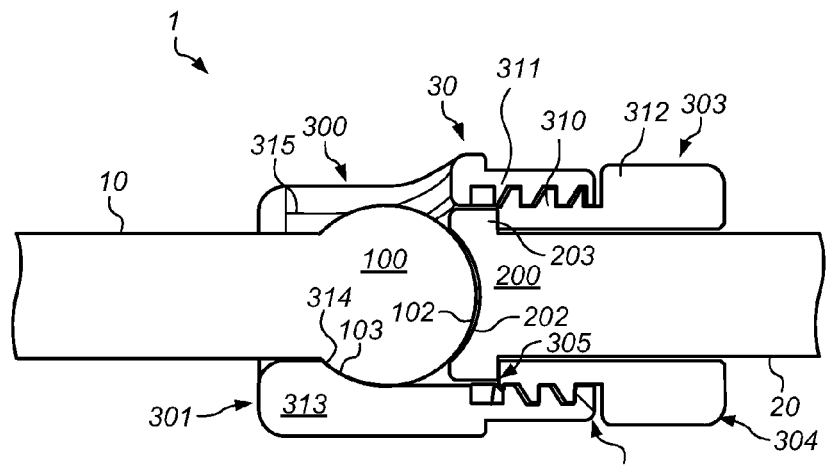
FIG. 2B is a cross-sectioned side view of an adjustable linkage depicted in a locked position in accordance with one or more embodiments of the present technique.

FIG. 1 illustrates an adjustable linkage 1 in accordance with one or more embodiments of the present technique. FIG. 2A is a cross-sectioned side view of adjustable linkage 1 depicted in an unlocked position and FIG. 2B is a cross-sectioned side view of adjustable linkage 1 depicted in a locked position in accordance with one or more embodiments of the present technique. In some embodiments, adjustable linkage 1 includes first elongated member 10 coupled to second elongated member 20 via locking mechanism 30. In some embodiments, first and second elongated members 10 and 20 are provided with a uniform circular cross-section. For example, in the illustrated embodiment, elongated members 10 and 20 include cylindrical rod shaped members. Elongated members 10 and 20 may be any suitable shape or size. Elongated members 10 and 20 may be straight, curved, or a combination of both. For example, in the illustrated embodiment, first and second elongated members 10 and 20 are substantially straight. Locking mechanism 30 may couple a proximal end 100 of first elongated member 10 to a proximal end 200 of second elongated member 20 (see FIGS. 2A and 2B). In some embodiments, distal ends of elongated members 10 and 20 opposite proximal ends 100 and 200 may be coupled to one or more bone portions. For example, as depicted and described below with respect to FIG. 3A, a distal end 101 of first elongated member 10 may be coupled to a bone portion that is superior to the bone portion to which a distal end 201 of second elongated member 20 is coupled. Although first and second elongated members 10 and 20 are referenced individually herein, it is understood that the features of these elongated members may be interchangeable. For example, distal end 201 of second elongated member 20 may be coupled to a bone portion that is superior to the bone portion to which a distal end 101 of first elongated member 10 is coupled.

Figure 2C:
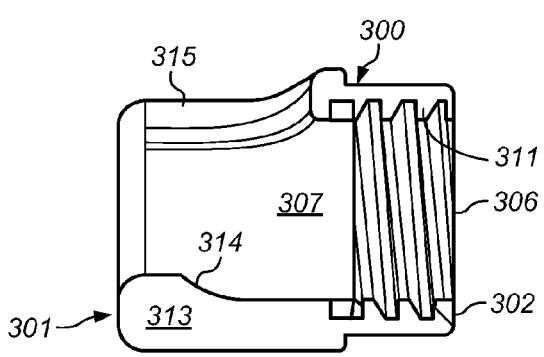
FIG. 2C is a cross-sectioned side view of a body of an adjustable linkage in accordance with one or more embodiments of the present technique.
Figure 2D:
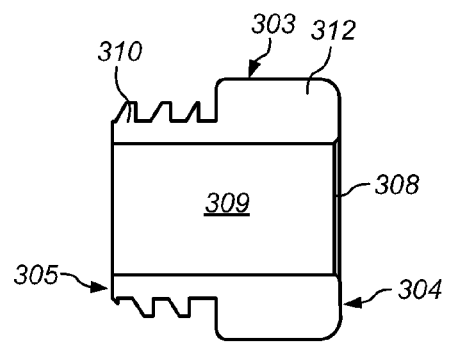
FIG. 2D is a cross-sectioned side view of a securing member of an adjustable linkage in accordance with one or more embodiments of the present technique.

Locking mechanism 30 may be adjustable from an unlocked position, as depicted in FIG. 2A to a locked position (and vice versa), as depicted in FIG. 2B. In some embodiments, providing locking mechanism 30 in an unlocked position may facilitate movement of elongated members 10 and 20 relative to one another, and providing locking mechanism 30 in a locked position may inhibit and/or prevent movement of elongated members 10 and 20 relative to one another. In some embodiments, locking mechanism 30 may include a body and a securing member. For example, in the illustrated embodiment, locking mechanism 30 includes a body 300 having a distal end 301 and proximal end 302, and a securing member 303 having distal end 304 and proximal end 305. Body 300 may include opening 306 defining an internal space 307 (see FIG. 2C). In some embodiments, opening 306 includes a through-hole that extends completely through a length of body 300. For example, in the illustrated embodiment, opening 306 defines space 307 extending from distal end 301 to proximal end 302 of body 300. Opening 306 may be of an appropriate size to receive a portion of first elongated member 10 and/or a portion of securing member 303. For example, in the illustrated embodiment, the portion of opening 306 near proximal end 302 includes an internally threaded hole complementary to an externally threaded proximal end 305 of securing member 303. Securing member 303 may include an opening 308 defining an internal space 309 (see FIG. 2D). Opening 308 may be of an appropriate size to receive a portion of second elongated member 20. In some embodiments, opening 308 includes a through-hole that extends completely through a length of securing member 303. For example, in the illustrated embodiment, opening 308 defines space 309 extending from distal end 304 to proximal end 305 of securing member 303, in which second elongated member 20 may be received (see FIGS. 2A and 2B).

In some embodiments, proximal end 100 of first elongated member 10 and/or proximal end 200 of second elongated member 20 may be positioned within internal space 307 of body 300 during use. For example, in the illustrated embodiments, proximal ends 100 and 200 of first and second elongated members 10 and 20 are both positioned within internal space 307 of securing member 303, with member 200 extending into and through internal space 309 of opening 308 of securing member 303.

In some embodiments, proximal end 100 includes convex surfaces 102 and 103. For example, in the illustrated embodiment, proximal end 100 terminates into a spherical shape defining convex surfaces 102 and 103. Proximal end 100 of first elongated member 10 may be any suitable shape. In some embodiments, proximal end 200 includes concave surface 202. For example, in the illustrated embodiment, proximal end 200 terminates into a convex recess that defines concave surface 202. Proximal end 200 of second elongated member 20 may be any suitable shape. In some embodiments, surface 202 is shaped at least substantially complementary to surface 102 of proximal end 100 of first elongated member 10.

In some embodiments, proximal end 305 of securing member 303 includes external threads 310, and a portion (e.g., proximal end 302) of opening 306 of body 300 includes internal threads 311. External threads 310 may be mated with internal threads 311 during use, such that body 300 and the securing member 303 are co-axially coupled to one another. In some embodiments, locking mechanism 30 may be adjusted from an unlocked position to the locked position, or vice versa, by advancing (e.g., threading) securing member 303 axially through opening 302 of body 300 via the mated threads. For example, body 300 and securing member 303 may be rotated relative to one another to engage threads 310 and 311, thereby providing for linear advancement or retraction of securing member 303 within opening 306 of body 300. In some embodiments, securing member may 303 further include a head 312 located at or proximate distal end 304. Securing member 303 may be advanced through, or retracted from, opening 306 of body 300 by applying a rotational torque to head 312 when external threads 310 are mated with internal threads 311. For example, an open-end socket wrench or similar tool may be used to engage and torque head 312, thereby rotating securing member 303. Rotation/torque may be reversed to facilitate unlocking of locking mechanism 30. Although locking mechanism 30 depicted in FIGS. 2A-2D includes a threaded engagement between body 300 and securing member 303 for adjusting locking mechanism 30 between unlocked and locked positions, any known means of facilitating such an adjustment may be used. For example, a locking mechanism may include one or more detent features, rails and/or rollers to facilitate adjustment of locking mechanism 30 between unlocked and locked positions.

In some embodiments, second elongated member 20 may include a radial flange 203 located at or near proximal end 200. During use, proximal end 305 of securing member 303 may abut radial flange 203 such that, as securing member 303 is advanced through opening 306 of body 300, surface 202 is urged towards surface 102. Thus, linear advancement of securing member 303 into opening 306 may result in linear advancement of second elongated member 20 toward/into opening 306 and/or into contact with first elongated member 10.

In some embodiments, body 300 may include a retaining portion 313 located near distal end 301. Retaining portion 313 may define an inner surface 314 for retaining first elongated member 10 within opening 306 during use. For example, in the depicted embodiment, inner surface 314 is at least partially concave and shaped at least substantially complementary to convex surface 103 of proximal end 100. Retaining portion 313 may inhibit dislodgment of first elongated member 10 from internal space 307. In some embodiments, inner surface 314 may extend around at least a majority (e.g., about fifty, sixty, seventy, eighty, ninety percent or more) of proximal end 100 during use. For example, as depicted in FIG. 1, inner surface 314 (see FIG. 2B) extends about three-hundred thirty degrees around an exterior of proximal end 100, having a slot cut-out 315 in the remaining thirty degrees around the exterior of proximal end 100.

In some embodiments, body 300 may include a slot cut-out 315 extending from distal end 301 towards proximal end 302 and located radially opposite and/or adjacent to retaining portion 313. Slot cut-out 315 may be of an appropriate size to receive a portion of second elongated member 10. Slot cut-out 315 may inhibit dislodgment of first elongated member 10 from internal space 307. More specifically, the width of slot cut-out 315 may be less than the effective diameter of proximal end 100 of elongated member 10.

When locking mechanism 30 is in an unlocked position, as depicted in FIG. 2A, relative movement is permitted between first and second elongated members 10 and 20, body 300 and securing member 303. For example, first elongated member 10 is angularly movable relative to second elongated member 20 when locking mechanism 30 is in an unlocked position. Likewise, second elongated member 20 is angularly movable relative to first elongated member 10. In some embodiments, elongated members 10 and 20 are angularly movable in three planes relative to one another. For example, first and second elongated members 10 and 20 may be pivoted relative to one another such that the longitudinal axis extending through each of first and second elongated members 10 and 20 are oriented at an angle (e.g., oblique) to one another.

FIG. 1 portrays the relative angular movement of the elongated members when the locking mechanism is in the unlocked position. More specifically, FIG. 1 depicts planes 60a, 60b, and 60c centered about axes 6a, 6b, and 6c respectively. Possible relative movement between first and second elongated members 10 and 20 is indicated by arrows 600a, 600b, and 600c. For example, elongated members 10 and 20 may be rotated about axis 6c, elongated member 10 may be rotated into slot cut-out 315 toward axis 6a such that the longitudinal axis of elongated members 10 and 20 are oriented at an angle relative to one another, and/or body 300 may be rotated relative to head 312 and/or elongated member 20 such that slot cut-out 315 is rotated toward axis 6b, thereby enabling elongated rod member 10 to be rotated about axis 6c (e.g., from a vertical position substantially parallel to axis 6a to a horizontal position substantially parallel to axis 6b).

When locking mechanism 30 is provided in the locked position, as depicted in FIG. 2B, relative movement between first and second elongated members 10 and 20, body 300 and securing member 303 may be inhibited. In some embodiments, the relative angular position of elongated members 10 and 20 is substantially fixed when locking mechanism 30 is provided in the locked position. Elongated members 10 and 20 may be held in place via frictional interfaces between adjacent/abutting surfaces in compressive contact with one another as a result of advancing securing element 303 into opening 306 of body 300. For example, securing member 303 may be held by force in direct connection with body 300 via mating of threads 310 and 311; radial flange 203 may be held by force in direct connection with proximal end 305 of securing member 303; convex surface 102 of first elongated member 10 may be held by force in direct connection with complementary shaped concave surface 202 of second elongated member 20; and convex surface 103 of first elongated member 10 may be held by force in direct connection with complementary shaped concave surface 314 of body 300.

Figure 3A:
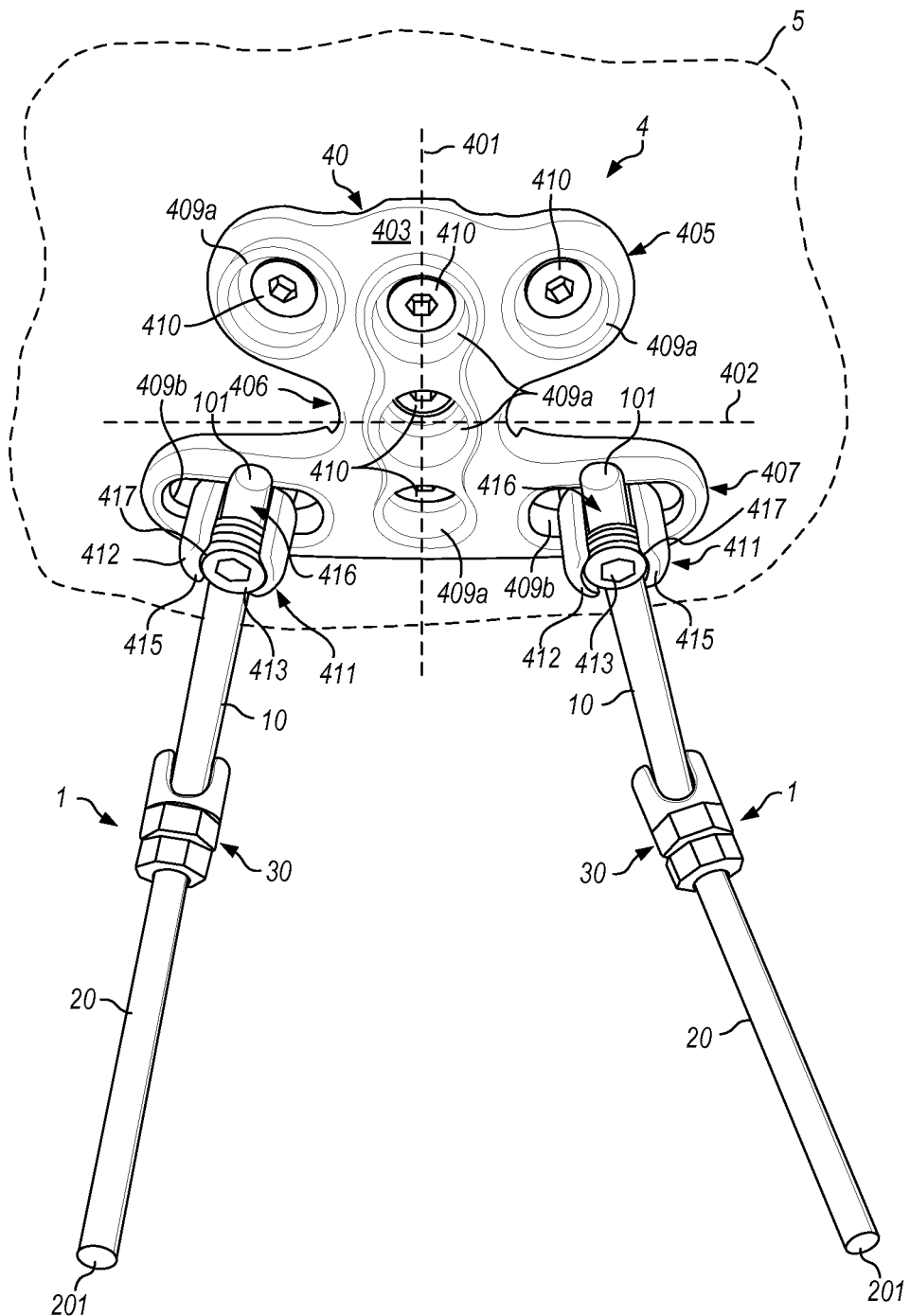
FIG. 3A is a perspective view of an apparatus for coupling bone portions in accordance with one or more embodiments of the present technique.
Figure 3B:
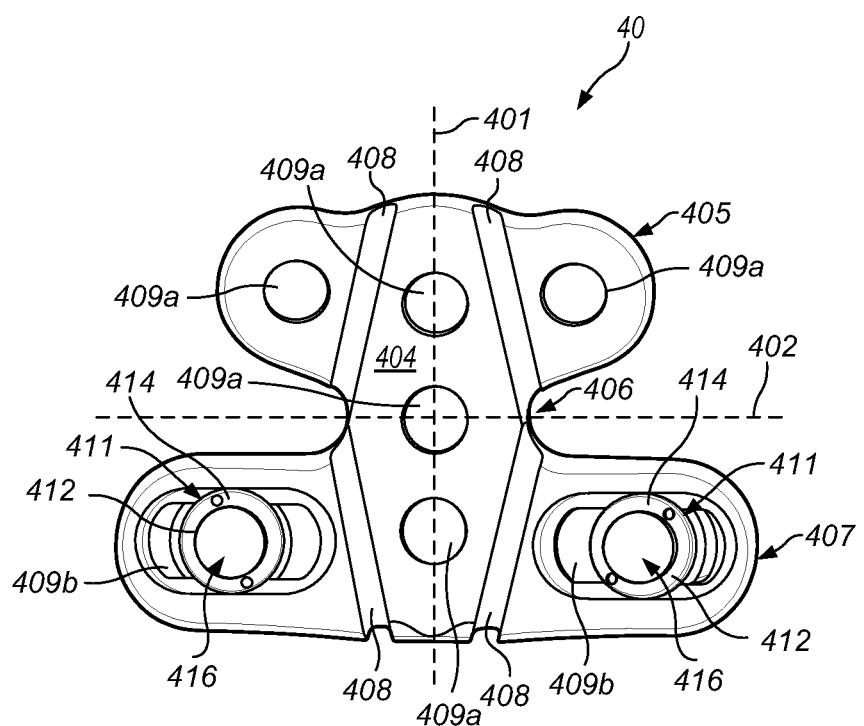
FIG. 3B is a view of the anterior surface of the plate depicted in FIG. 3A in accordance with one or more embodiments of the present technique.

FIG. 3A illustrates a perspective view of an apparatus 4 for coupling bone portions in accordance with one or more embodiments of the present technique. Such an apparatus may be suitable for coupling two or more vertebrae following a bone grafting procedure. In the illustrated embodiment, apparatus 4 includes adjustable linkages 1 coupled to a plate 40 via members 10. In some embodiments, plate 40 includes a vertical midline 401 and horizontal midline 402, as well as a posterior surface 403 and an anterior surface 404 (see FIG. 3B). Posterior surface 404 may be coupled to a bone portion 5 (for clarity, only a local section of bone portion 5 is shown). In some embodiments, plate 40 may be configured for coupling on or near the occipital region of a patient's skull. For example, plate 40 may include an occipital plate and bone portion 5 may include a lower rear portion of the skull. In other embodiments, plate 40 may be of any suitable type or configuration. In some embodiments, plate 40 may include a superior portion 405, a medial portion 406, and/or an inferior portion 407. Medial portion 406 may be provided with a lesser lateral thickness (e.g., with) than both superior portion 405 and inferior portion 407 to facilitate bending of the plate at or near horizontal midline 402. Plate 40 may include one or more grooves 408 located on anterior surface 404 and/or posterior surface 403 of plate 40 and positioned longitudinally thereon (see FIG. 3B). In some embodiments, grooves 408 may be provided on either side of vertical midline 401. Grooves 408 may facilitate bending of the lateral sides of the plate 40. For example, plate 40 may be bent into a shape that is shaped complementary to a curvature of bone portion 5. Each of the superior, medial, and inferior portions 405, 406, and 407 may include apertures 409a. Apertures 409a may include openings (e.g., through holes) that receive mechanical fasteners 410 for coupling plate 40 to bone portion 5. In some embodiments, apertures 409a may include a countersunk portion (e.g., from posterior surface 403) to decrease the anterior-posterior thickness of the plate. In some embodiments, inferior portion 407 may include laterally elongated apertures 409b. Coupling elements 411 may be disposed in apertures 409b and coupled to plate 40. Coupling elements 411 may include attachment bodies 412 and locking screws 413 disposable therein. Attachment bodies 412 may include an anterior surface 414, posterior surface 415, and openings 416 Coupling element 411 may include a U-shaped member where opening 416 includes a slot 417 extending into anterior surface 414. Slot 417 may be sized to accept first elongated member 10 disposed laterally therein, as depicted in FIG. 3A. Openings 416 may include a through hole that extends from posterior surface 415 to anterior surface 414. During use, coupling elements 411 may couple distal ends 101 of elongated members 10 to plate 40. For example, during use, distal ends 101 of elongated members 10 may be inserted into slot 417 of openings 416 and fixedly held in place by locking screws 413.

In some embodiments, apparatus 4 may further include mechanical fasteners for coupling distal ends 201 of second elongated member 20 to bone portions. For example, the bone portions may include posterior surfaces of one or more vertebrae located within the vertebral column. In some embodiments, distal ends 201 may be coupled to a bone fastener fastened to a posterior surface of a vertebrae or other bony structure.

The apparatus for coupling bone portions described herein may include at least one adjustable linkage having a first elongated member, a second elongated member, and a locking mechanism. The locking mechanism may be configured to couple the first and second elongated members such that the elongated members are angularly movable in three planes relative to one another. Thus, the apparatus may be highly adaptable to the anatomy of a patient during use. Additionally, in some embodiments, the surfaces of the coupled elongated members are directly connected when the locking mechanism is in the locked position. For example, elongated members may directly contact one another to generate a frictional interface that inhibits relative movement between to the elongated members. A direct connection of the coupled members provides a relatively small linking joint and may be less intrusive when the apparatus is implanted within the body of a patient.

In some embodiments, one or more of the elements described above are included in a bone fixation kit. In certain embodiments, one or more of the elements described above are included in an occipital-cervical fixation kit. For example, an occipital-cervical fixation kit may include some or all of the components depicted in FIG. 3A. One or more of the elements in the kits may be coupled or provided separately. Further, any coupled elements may be arranged in any suitable configuration, including the configurations described above.

A method of coupling bone portions may include coupling the proximal end of a first elongated member to the proximal end of a second elongated member such that the first and second elongated members are angularly movable relative to one another. In some embodiments, the first and second elongated members are angularly movable in three planes relative to one another. In some embodiments, the proximal ends of the first and second elongated members are coupled via a locking mechanism. In such embodiments, coupling the proximal end of a first elongated member to the proximal end of a second elongated member may include disposing at least the respective proximal ends of the first and second elongated members within the internal space of a body and/or a securing member of the locking mechanism and coupling the securing member to the body such that the locking mechanism is in an unlocked position. Coupling the securing member to the body may include mating a set of internal threads of the body with a set of external threads of the securing member. In some embodiments, the securing member and the body are co-axially coupled.

A method of coupling bone portions may further include, coupling the distal end of the first elongated member to a first bone portion and angularly adjusting the second elongated member with respect to the first elongated member such that the second elongated member is positioned at a selected angular position relative to the first elongated member. In some embodiments, coupling the distal end of the first elongated member to a first bone portion includes coupling a plate to the first bone portion and coupling the distal end of the first elongated member to the plate. In certain embodiments, the first bone portion is in or near the occipital region of the patient's skull and the plate is an occipital plate. In one embodiment, coupling the distal end of the first elongated member to a first bone portion further includes deforming the occipital plate such that the anterior surface of the plate is shaped substantially complementary to the surface of the skull at or near the occipital region. In some embodiments, the selected angular position of the second elongated member relative to the first elongated member coincides with the anatomy of a patient.

A method of coupling bone portions may still further include directly connecting the proximal end of the second elongated member to the proximal end of the first elongated member such that relative movement between the elongated members is inhibited. In such embodiments, the method may include placing the locking mechanism in a locked position and/or adjusting the locking mechanism from an unlocked position to the locked position. Adjusting the locking mechanism from an unlocked position to a locked position may include advancing the securing member through an internal space of the body via a mating set of internal and external threads. In certain embodiments, relative movement between the elongated members is prevented.

A method of coupling bone portions may still further include coupling the distal portion of the second elongated member to a second bone portion.

What is claimed is:

1. An apparatus comprising:
a first elongated member comprising a distal end and a proximal end,
wherein the distal end of the first elongated member is couplable to a first bone portion during use;
a second elongated member comprising a distal end and a proximal end,
wherein the distal end of the second elongated member is couplable to a second bone portion during use,
wherein the proximal end of the second elongated member comprises a surface that is shaped complementary to a surface of the proximal end of the first elongated member;
a locking mechanism coupling the proximal end of the first elongated member to the proximal end of the second elongated member, wherein the locking mechanism comprises a body and a securing member, wherein a portion of the securing member comprises a set of external threads and a portion of the body comprises a mating set of internal threads such that, during use, the locking mechanism is adjusted from the unlocked to the locked position by advancing the securing member axially through the internal space of the body via the mating threads, wherein the proximal ends of the first and second elongated members are positioned in the body during use, wherein the securing member engages at least one of the first elongated member, the second elongated member, and the body when the locking mechanism is in a locked position, wherein the body and securing member comprise respective openings defining respective internal spaces, and wherein, during use, at least the respective proximal ends of the first elongated member and the second elongated member are disposed within the internal space of the body and/or the securing member, and wherein the body comprises an opening coupled to the respective opening in the body such that the first elongated member is positionable, during use, in the opening such that the first elongated member is oriented at an angle relative to the second elongated member, wherein the locking mechanism is adjustable from an unlocked position to the locked position such that, when the locking mechanism is in the unlocked position, the first elongated member is angularly movable relative to the second elongated member, the first elongated member is independently rotatable about a first longitudinal axis and a second longitudinal axis, and the second elongated member is independently rotatable about a third longitudinal axis, and when the locking mechanism is in the locked position, the complementary shaped surfaces of the first elongated member and the second elongated member are directly connected and the relative angular position of the first elongated member and the second elongated member is substantially fixed.

2. The apparatus of claim 1, wherein the first elongated member is angularly movable in three planes relative to the second elongated member when the locking mechanism is in the unlocked position.

3. The apparatus of claim 1, further comprising a plate coupled to the distal end of the first elongated member and couplable to a portion of the first bone portion during use.

4. The apparatus of claim 3, wherein the plate is an occipital plate and the first bone portion comprises a portion of a skull.

5. The apparatus of claim 3, wherein the plate comprises a longitudinally positioned groove located on the anterior surface of the plate.

6. The apparatus of claim 1, wherein the surface of the first elongated member is substantially convex and the surface of the second elongated member shaped complementary to the first elongated member is substantially concave.

7. The apparatus of claim 1, wherein the body comprises a retaining portion inhibiting the dislodgment of at least the first elongated member from the internal space of the body.

8. The apparatus of claim 7, wherein the retaining portion comprises a surface that is complementary to a surface of the proximal end of the first elongated member.

9. The apparatus of claim 1, wherein the body comprises a slot extending from one end of the body towards the other end of the body, and wherein, during use, a portion of the first elongated member is received by the slot.

10. An apparatus comprising:

a first elongated member comprising a distal end and a proximal end, wherein the distal end of the first elongated member is couplable to a first bone portion during use;

a second elongated member comprising a distal end and a proximal end, wherein the distal end of the second elongated member is couplable to a second bone portion during use, wherein the proximal end of the second elongated member comprises a surface that is shaped complementary to a surface of the proximal end of the first elongated member;

a locking mechanism coupling the proximal end of the first elongated member to the proximal end of the second elongated member, wherein the locking mechanism comprises a body and a securing member, wherein the second elongated member comprises a flange located such that, during use, as the locking mechanism is adjusted from the unlocked position to the locked position, a portion of the securing member abuts the flange and urges the complementary surface of the second elongated member towards the complementary surface of the first elongated member, wherein the proximal ends of the first and second elongated members are positioned in the body during use, wherein the securing member engages at least one of the first elongated member, the second elongated member, and the body when the locking mechanism is in a locked position, wherein the body and securing member comprise respective openings defining respective internal spaces, and wherein, during use, at least the respective proximal ends of the first elongated member and the second elongated member are disposed within the internal space of the body and/or the securing member, and wherein the body comprises an opening coupled to the respective opening in the body such that the first elongated member is positionable, during use, in the opening such that the first elongated member is oriented at an angle relative to the second elongated member, wherein the locking mechanism is adjustable from an unlocked position to the locked position such that, when the locking mechanism is in the unlocked position, the first elongated member is angularly movable relative to the second elongated member, the first elongated member is independently rotatable about a first longitudinal axis and a second longitudinal axis, and the second elongated member is independently rotatable about a third longitudinal axis, and when the locking mechanism is in the locked position, the complementary shaped surfaces of the first elongated member and the second elongated member are directly connected and the relative angular position of the first elongated member and the second elongated member is substantially fixed.

11. The apparatus of claim 10, wherein the first elongated member is angularly movable in three planes relative to the second elongated member when the locking mechanism is in the unlocked position.

12. The apparatus of claim 10, further comprising a plate coupled to the distal end of the first elongated member and couplable to a portion of the first bone portion during use.

13. The apparatus of claim 12, wherein the plate is an occipital plate and the first bone portion comprises a portion of a skull.

14. The apparatus of claim 12, wherein the plate comprises a longitudinally positioned groove located on the anterior surface of the plate.

15. The apparatus of claim 10, wherein the surface of the first elongated member is substantially convex and the surface of the second elongated member shaped complementary to the first elongated member is substantially concave.

16. The apparatus of claim 10, wherein the body comprises a retaining portion inhibiting the dislodgment of at least the first elongated member from the internal space of the body.

17. The apparatus of claim 16, wherein the retaining portion comprises a surface that is complementary to a surface of the proximal end of the first elongated member.

18. The apparatus of claim 10, wherein the body comprises a slot extending from one end of the body towards the other end of the body, and wherein, during use, a portion of the first elongated member is received by the slot.

\* \* \* \* \*